US011337603B2

(12) United States Patent
Fowler et al.

(10) Patent No.: US 11,337,603 B2
(45) Date of Patent: May 24, 2022

(54) LAPAROSCOPIC DEVICE IMPLANTATION AND FIXATION SYSTEM AND METHOD

(71) Applicant: Platform Imaging, LLC, New York, NY (US)

(72) Inventors: Dennis L. Fowler, Overland Park, KS (US); Thomas F. McNall, Wakefield, MA (US); Nathan E. Wallace, Windham, NH (US); Daniel H. Hammerle, Danvers, MA (US); Marc Daigle, Concord, MA (US)

(73) Assignee: PLATFORM IMAGING, LLC, New York, NY (US)

( * ) Notice: Subject to any disclaimer, the term of this patent is extended or adjusted under 35 U.S.C. 154(b) by 346 days.

(21) Appl. No.: 15/973,588

(22) Filed: May 8, 2018

(65) Prior Publication Data

US 2018/0317762 A1 Nov. 8, 2018

Related U.S. Application Data

(60) Provisional application No. 62/503,030, filed on May 8, 2017.

(51) Int. Cl.
*A61B 90/00* (2016.01)
*A61B 17/34* (2006.01)
(Continued)

(52) U.S. Cl.
CPC ........ *A61B 1/3132* (2013.01); *A61B 1/00128* (2013.01); *A61B 1/00147* (2013.01);
(Continued)

(58) Field of Classification Search
CPC ................ A61B 1/0661; A61B 1/3132; A61B 17/00234; A61B 2017/003; A61B 2017/347–348; A61B 2017/3492
See application file for complete search history.

(56) References Cited

U.S. PATENT DOCUMENTS 4,651,201 A 3/1987 Schoolman
4,976,721 A 12/1990 Blasnik
(Continued)

FOREIGN PATENT DOCUMENTS

JP 2000175865 A 6/2000

OTHER PUBLICATIONS

PCT Search Report, dated Sep. 10, 2018, pp. 1-12, USA.
EP Partial Search Report, dated Jan. 19, 2021, 13 pages, European Patent Office, DE.

*Primary Examiner* — Matthew J Kasztejna
(74) *Attorney, Agent, or Firm* — John M. Griem, Jr.; Carter Ledyard & Milburn, LLP.

(57) ABSTRACT

Devices used during minimally invasive surgery (sometimes called minimal access surgery or laparoscopic surgery) for implantation and fixation of various cameras, for example, to the human body. An insertable device including a housing divided into two sections, a camera, a sensor, at least two LED lights, a lens flush located above the camera lens to clean a lens of the camera, and a motor for moving the camera in relation to the housing with pan and tilt capabilities. An insertion tool for inserting devices including a cannula, a top housing, and a bottom, wherein the bottom couples with the insertable device. A capture and fixation device for capturing and fixing an insertable device to an internal body cavity wall, the device includes a cannula, at least one slideable clamp device, and a retractable loop. Once the insertable device is positioned, the retractable loop fixes the insertable device to the body cavity wall.

14 Claims, 11 Drawing Sheets

(51) Int. Cl.
*A61B 1/313* (2006.01)
*A61B 17/00* (2006.01)
*A61B 1/04* (2006.01)
*A61B 1/00* (2006.01)
*A61B 90/30* (2016.01)
*A61B 1/06* (2006.01)

(52) U.S. Cl.
CPC .......... *A61B 1/00183* (2013.01); *A61B 1/041* (2013.01); *A61B 17/00234* (2013.01); *A61B 90/361* (2016.02); *A61B 1/0661* (2013.01); *A61B 17/3421* (2013.01); *A61B 2017/003* (2013.01); *A61B 2017/00283* (2013.01); *A61B 2017/00358* (2013.01); *A61B 2017/00473* (2013.01); *A61B 2017/00477* (2013.01); *A61B 2017/00876* (2013.01); *A61B 2090/309* (2016.02)

(56) References Cited

U.S. PATENT DOCUMENTS

| | | | |
|---|---|---|---|
| 5,147,316 A * | 9/1992 | Castillenti | A61B 17/34 604/164.04 |
| 5,279,575 A * | 1/1994 | Sugarbaker | A61B 17/3403 604/104 |
| 5,330,497 A * | 7/1994 | Freitas | A61B 17/34 604/164.12 |
| 5,334,185 A * | 8/1994 | Giesy | A61B 17/3415 604/170.01 |
| 5,395,374 A | 3/1995 | Miller et al. | |
| 5,604,531 A | 2/1997 | Iddan et al. | |
| 5,795,308 A | 8/1998 | Russin | |
| 6,428,469 B1 | 8/2002 | Iddan et al. | |
| 6,540,738 B2 * | 4/2003 | Kurfess | A61B 17/3415 600/114 |
| 8,225,798 B2 * | 7/2012 | Baldwin | A61B 17/2909 128/898 |
| 8,435,174 B2 * | 5/2013 | Cropper | A61B 17/3421 600/203 |
| 8,460,186 B2 * | 6/2013 | Ortiz | A61B 17/3421 600/216 |
| 9,033,957 B2 | 9/2015 | Cadeddu et al. | |
| 9,155,550 B2 * | 10/2015 | Shipp | A61B 17/3421 |
| 9,393,076 B2 | 7/2016 | Fowler et al. | |
| 9,730,761 B2 | 8/2017 | Fowler et al. | |
| 10,390,694 B2 * | 8/2019 | Farin | A61B 1/053 |
| 2002/0042562 A1 | 4/2002 | Meron et al. | |
| 2003/0225423 A1 | 12/2003 | Huitema | |
| 2005/0288555 A1 | 12/2005 | Binmoeller | |
| 2008/0015413 A1 * | 1/2008 | Barlow | A61B 1/273 600/114 |
| 2008/0312500 A1 | 12/2008 | Asada et al. | |
| 2010/0010294 A1 | 1/2010 | Conlon et al. | |
| 2010/0081875 A1 | 4/2010 | Fowler et al. | |
| 2011/0046440 A1 * | 2/2011 | Asada | A61B 1/00124 600/104 |
| 2014/0018732 A1 | 1/2014 | Bagaoisan et al. | |
| 2015/0025310 A1 | 1/2015 | Everingham et al. | |
| 2015/0142041 A1 | 5/2015 | Kendale et al. | |
| 2016/0354083 A1 | 12/2016 | Sengun | |

\* cited by examiner

LAPAROSCOPIC DEVICE IMPLANTATION AND FIXATION SYSTEM AND METHOD

This application claims priority to U.S. Provisional Patent Application No. 62/503,030, filed May 8, 2017, entitled "Improved Laparoscopic Device Implantation and Fixation System and Method" and is hereby incorporated by reference in its entirety.

FIELD OF THE INVENTION

The present invention relates to a system of related devices used during surgery. More specifically the present invention relates to devices used during minimally invasive surgery (sometimes called minimal access surgery or laparoscopic surgery) for implantation and fixation of various cameras to the human body.

BACKGROUND OF THE INVENTION

Minimally invasive surgical procedures, e.g., laparoscopic procedures, have dramatically reduced patient recovery times. However, the reduced recovery times have correspondingly resulted in an increase, from a surgeon's perspective, in the complexity of the surgical procedures. This is in part due to the characteristic relatively small incisions, e.g., approximately 10 mm in diameter, through which a surgeon accesses a surgical site to perform the minimally invasive surgery. The limited access adds to the complexity of the surgical procedures since surgeons must remotely manipulate sufficiently small instruments though the incisions and must also view the surgical site through the small incisions.

Imaging systems that provide a view of the surgical site for a minimal access surgical procedure typically include an endoscope, e.g., a tubular instrument containing optical lenses and light guides that feed images to an external video camera and a monitor, such as the endoscope discussed in U.S. Pat. No. 4,651,201. Endoscopes, however, have drawbacks. For instance, since the surgeon is generally using both hands to manipulate other instruments used in the procedure, e.g., forceps, scissors, coagulators/cauterizer probes, etc., an assistant is required to hold and orient the endoscope to adjust the view during the procedure. Robotics have recently been introduced to automate the task of orienting the endoscope during minimally invasive surgical procedures, such as the Automated Endoscopic System for Optimal Positioning ("AESOP"). The AESOP uses a robot arm that is directed by spoken commands to orient the endoscope. While the AESOP takes the burden off the assistant and provides a much more stable view of the field, the equipment necessary for the AESOP is complex and occupies a large part of the operating room floor. AutoLap is another system currently on the market, providing an image-guided robotic laparoscopic positioning system. AutoLap interacts with the surgeon's movements in the surgical cavity, guiding the robotic laparoscopic positioner in real time. However, AutoLap still requires a scope to be inserted for the entire duration and the trocar cannula cannot be used for an additional instrument. Therefore, multiple patient incisions are required. In addition, AutoLap requires additional equipment on the outside of the patient which is expensive and also may get in the surgeon's way.

A smaller and simpler robotic endoscope manipulator that can be placed directly over the insertion point was developed at the Institut National de Recherche en Informatique et en Automatiqueinria ("INRIA"). However, the INRIA system as well as other robotic systems fail to address the limited available range of motion about the fulcrum at the abdominal wall through which the endoscope as well as other instruments pass to gain access to the surgical site. The limited range of motion translates into limits with regard to the degree of freedom that the instruments may be oriented toward the surgical site.

Active or hyper endoscope systems have been proposed that generally consist of a multi-link robotic arm with a camera mounted thereon, such as the active endoscope discussed in Japanese Patent 2000175865, which is hereby incorporated herein by reference, which provides additional freedom with respect to orienting the endoscope camera. However, these systems require a dedicated incision for the endoscope to access the surgical site and typically require relatively high voltage to operate the actuators necessary to manipulate the hyper endoscope which from a safety perspective may be problematic when used in surgical procedures. Pill cameras have also been adopted for imaging sections of the small intestine that are out of the reach of a colonoscope, such as the pill camera described in U.S. Pat. Nos. 5,604,531 and 6,428,469. However, pill cameras do not generally include means for orienting the camera; rather, pill cameras merely rely on peristalsis to orient the camera.

Therefore there is a need for systems and devices for minimal access procedures that do not require an assistant to hold and orient an instrument and that provide additional or greater freedom than is provided with an endoscope or other instrument with regard to orienting the instrument toward the site of interest. There is also a need for systems and devices for minimal access procedures that provide additional or greater freedom with regard to orienting the instrument toward a site of interest than is provided with an active or hyper endoscope that do not require a dedicated access incision into the site for the instrument. Some prior art for fixing surgical tools to the human body internally, include U.S. Pat. No. 9,033,957 discloses a surgical anchor system having an opening and at least one pin to position and orient a surgical tool inside a human body. The surgical anchor is anchored to the lumen of the body cavity by insertion of a single small pin which may be attached providing a hands free anchor point for other tools whole also freeing up the trocar for insertion of additional anchors or providing for insertion of another working surgical tool.

U.S. Publication 2002/0042562 teaches an immobilized in vivo sensing device that has rings attached to it and uses the rings for sewing the device capsule to a desired location in the vicinity of the surgical site. U.S. Publication No. 2005/0288555 discloses a device and method for viewing internal body surfaces without an external attachment. The device is swallowed by the patient or placed with an endoscope and may be secured to the body using securement elements attached to the device such as a barbed hook, a loop or a tab. U.S. Publication 2008/0312500 discloses an endoscope system that includes a camera, a camera side magnet and a fixing magnet for fixing the camera within the abdominal cavity using fixing magnets and an adhesive layer.

The present invention is an improvement to prior art minimal access surgery devices such as U.S. Pat. No. 9,730,761, titled "Insertable Device and System for Minimal Access Procedure," filed Jan. 17, 2012, and U.S. Pat. No. 9,393,076, titled "Insertable Device and System for Minimal Access Procedure," incorporated by reference herein. Both U.S. Patents '076 and '761 teach a system including at least one insertable device. The insertable device having an elongated body, two actuators, and a camera. The '761 patent controlling the movement of the camera remotely by a control system. U.S. Patent '076 has a driving device communicatively connected to the insertable device. The driving device including at least one controller and an image tracking module for tracking the movement of at least one object in a field of view of the camera. Although fixing tools in the human body may be taught in the prior art, they do not teach the novel ideas of the present invention.

SUMMARY OF THE INVENTION

The present invention provides a capture and fixation device for capturing and fixing an insertable device to an internal body cavity wall, the device includes a cannula, wherein the cannula inserts into and/or through a body cavity wall, at least one slideable clamp device surrounding the cannula, and a retractable loop deployable through a plastic sheath passable through the cannula, wherein the retractable loop captures the insertable device and assists in positioning the insertable device, once the insertable device is positioned, the retractable loop fixes the insertable device to the body cavity wall.

The present invention also provides an insertion tool for inserting devices during a laparoscopic procedure, the tool includes a cannula, wherein the cannula encloses cables from an inserted device, a top housing, wherein the top housing encloses motors or printed circuit boards for driving the motors for the insertable device, and a bottom, wherein the bottom couples with the insertable device.

The present invention also provides an insertable device for use during a laparoscopic procedure. The insertable device includes a housing divided into two sections, a first housing and a second housing, a camera, the camera enclosed in the first housing wherein the first housing is moveable, a sensor, at least two LED lights, a lens flush located above the camera lens to clean a lens of the camera, and a motor for moving the camera in relation to the housing with pan and tilt capabilities, wherein the camera maintains the same horizon regardless of the camera position.

BRIEF DESCRIPTION OF THE DRAWINGS

A more detailed understanding of the invention may be had from the following description of a preferred embodiment, given by way of example and to be understood in conjunction with the accompanying drawing.

DETAILED DESCRIPTION

Figure 1A:
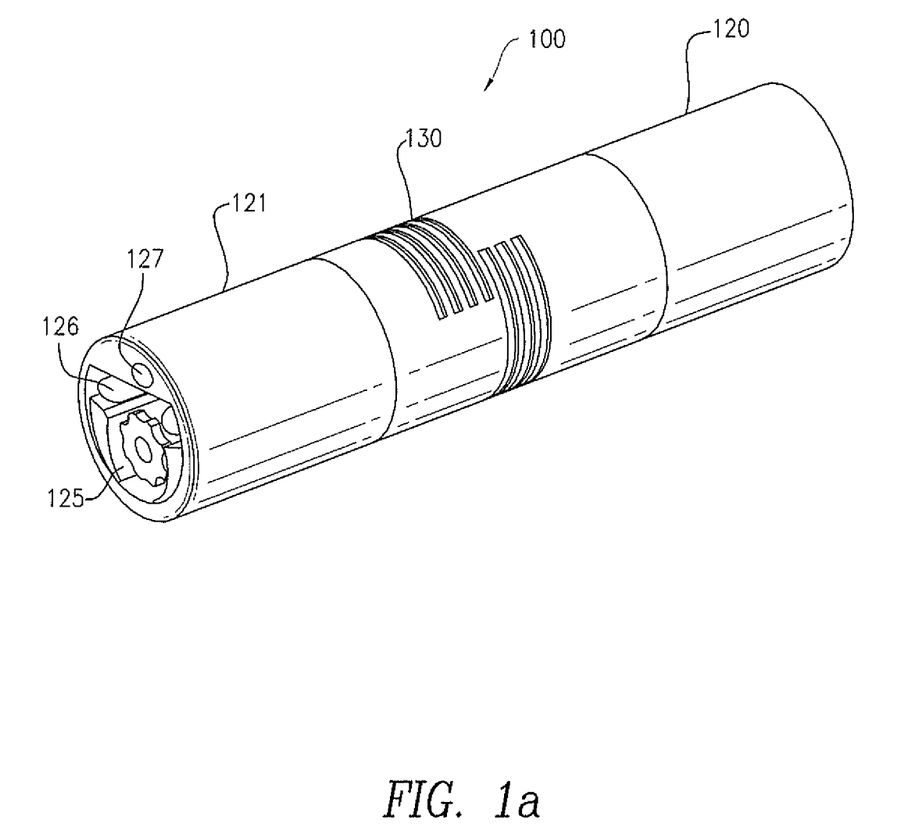
FIG. 1a shows an embodiment of an insertable device of the present invention.
Figure 1B:
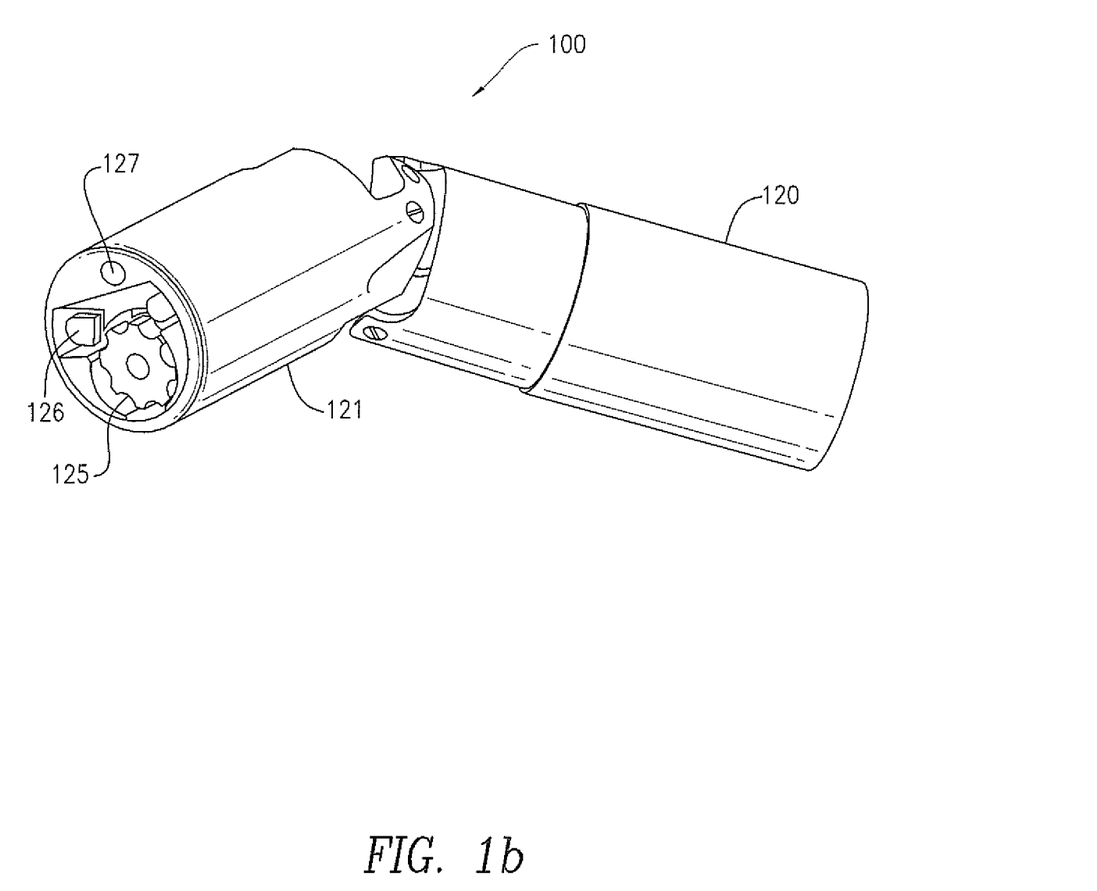
FIG. 1b shows the pan tilt capabilities of the insertable device.
Figure 2:
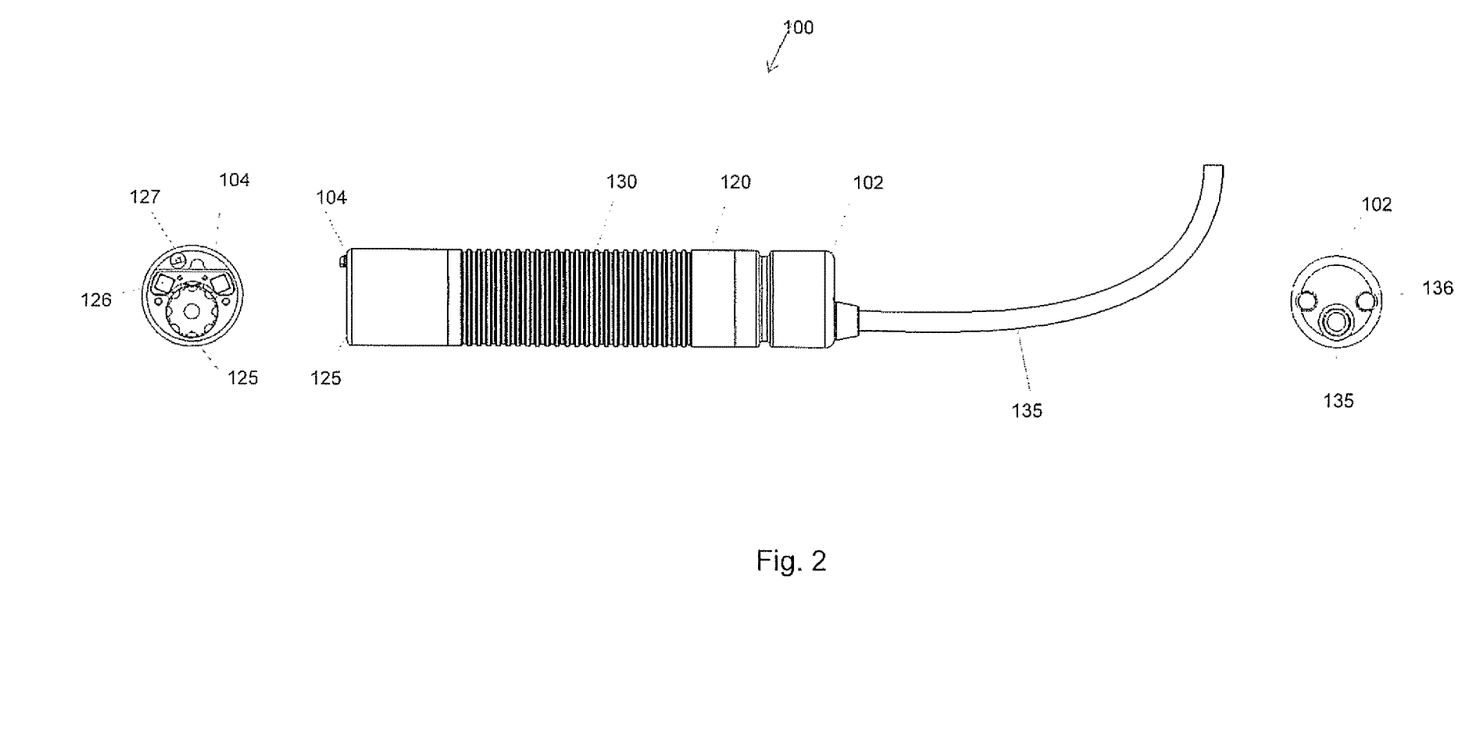
FIG. 2 shows another view of the insertable device.

The present invention includes an insertable device, an insertion tool, and a capture and fixation device. FIGS. 1a, 1b and 2 show insertable device 100 with a camera, for example. Insertable device 100 includes housing 120 that encloses camera 125, motors for moving camera 125 and lens flush 127 above camera 125. Camera 125 may be a high definition camera, has a sensor and provides LED illumination via at least 2 LEDs, 126. The use of multiple LEDS reduces shadows that result from a single LED. The motor provides a mechanism for moving camera 125 in relation to housing 120 with pan and tilt capabilities (as shown in FIG. 1b). The pan and tilt mechanism maintains the same horizon for camera 125 regardless of the pan or tilt position in contrast to prior art in which the horizon moves with the position of the camera. Lens flush 127 is located above the camera lens and sprays the lens with a sterile saline solution, when necessary, to keep the lens clear. Housing 120 is approximately 48 mm long in its entirety, for example. Camera 125 is enclosed in a moveable section 121 of housing 120 having a hinge. This allows camera 125 to move in line with the insertable device 100 during insertion, but can move up, down, left or right as necessary after insertion. Movable section 121 is approximately 19 mm long, for example, Camera 125 can provide an exploded view. FIG. 2 shows cabling 135 for insertable device 100 exiting out of the back 102 of insertable device 100. Cables 135 provide powering for the motor sensor and LEDs, as well as the source of saline solution for lens flush 127. Cables 135 also provide signal and image information to an exterior unit on a shelf with software, image processing, tool tracking software, test panel and interface and manual control for the pan/tilt mechanism. Back of device 102, also includes magnets, 136, used to secure insertable device 100 to an insertion tool.

Figure 3:
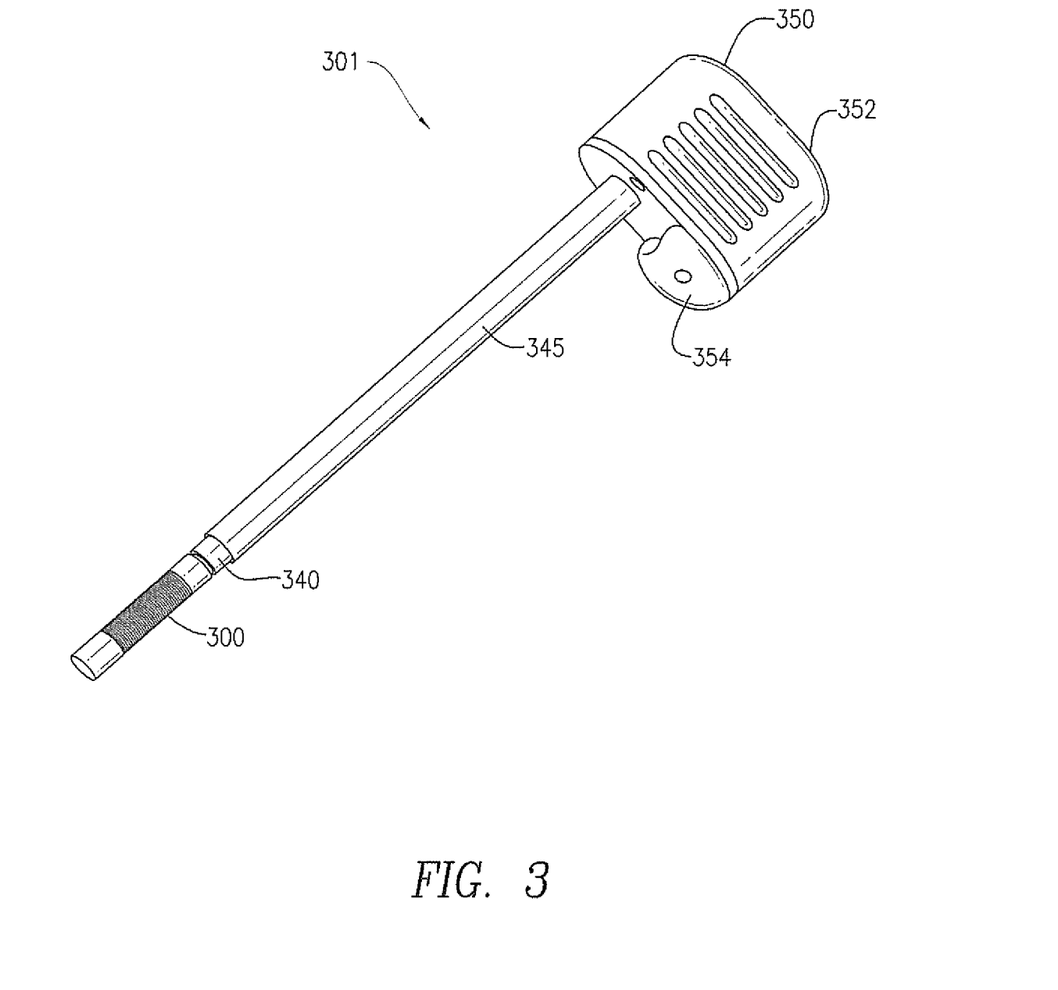
FIG. 3 shows an embodiment of an insertion tool of the present invention.

FIG. 3 shows an embodiment of an insertion tool 301 of the present invention. Insertion tool 301 includes a bottom 340, a top 350 and a cannula 345. Top 350 has top housing 352 and bottom housing 354. Insertion tool 301 provides housing for motor drive electronics as well as providing a channel for wires and tubes that connect to insertable device 300. Top housing 352 encloses the motor drive electronics. Top housing 352 dimensions may be approximately 46 mm long, 60 mm wide and has a 35 mm diameter, for example. The motor drive electronics may include driver boards for the pan and tilt motors. Insertable device 300 couples to bottom 340 of insertion tool 301.

Figure 4A:
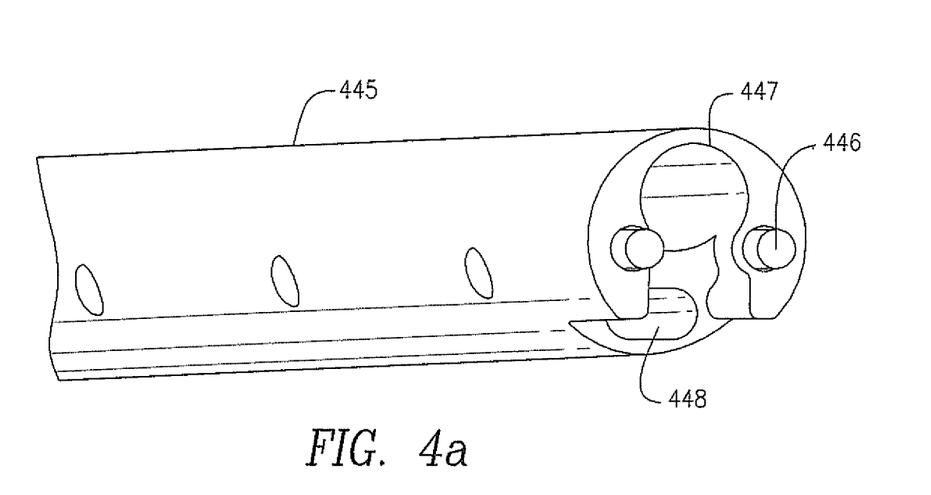
FIGS. 4a and 4b show the channels of the cannula and the top housing of the present invention.
Figure 4B:
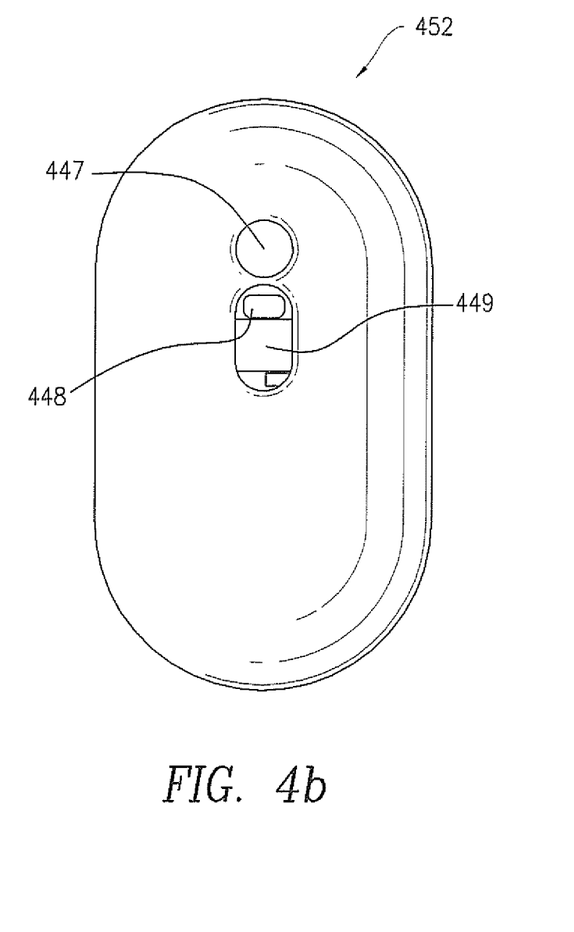
Figure 5:
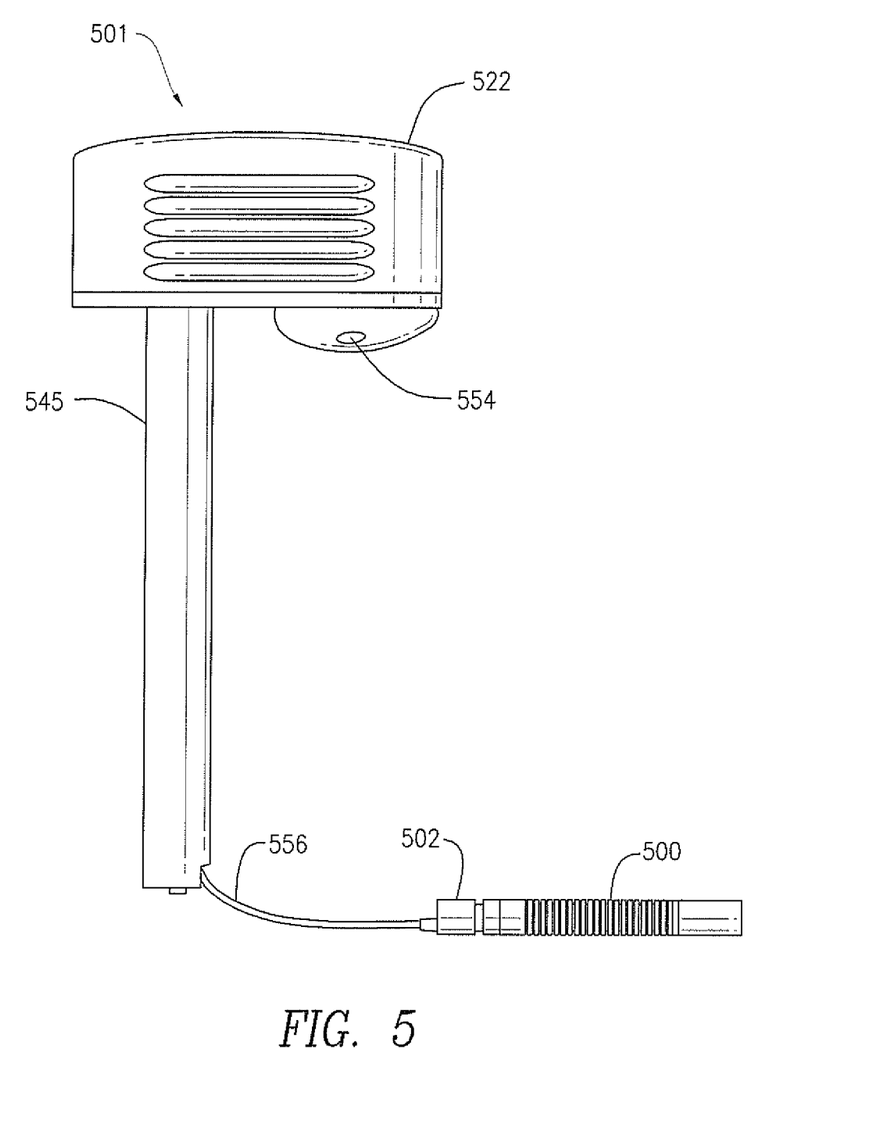
FIG. 5 shows cables connected to the insertion tool and insertable device.

Cannula 445 is split down the middle for easy assembly and houses two separate channels as seen in FIG. 4a, one for tooling, 447, and one for cables, 448. One channel, 448, houses the wires that deliver power to the motors and LED's, camera wires, and lens wash tubing, etc. while the other channel, 447, is used for insertion of a laparoscopic instrument during surgery. The laparoscopic instrument may vary in size from 3-5 mm. Cannula 445 may be approximately 150 mm in length with a 11 mm diameter, for example. FIG. 4b shows a top view of top housing 452 which has camera cable channel 448, tool channel 447 and motor drive service loop 449 based on a camera orientation being upward. For example, for the camera of an insertable device, channel 448 within cannula 445 houses the wires for connecting the camera, and carries wires for delivering power to the motors, LED's, and sensors of the camera. These wires can carry an image from the camera sensor and can carry a lens wash solution. As seen in FIG. 5, cables (wires, tubes, etc.) 556 continue out of the back 502 of insertion tool 500. Cables and wires 556 are used for lens wash, the camera and sensors and travel through cannula 545, exiting top housing 522 and connecting to a computer/power source or other external units to the surgical patient.

Wires and cables, 556, for motor power and signals exit the bottom of housing 554. Insertion tool 501 is compatible with 11 mm trocars, for example.

The insertion tool may have a seal, such as a silicone or other sealing membrane to prevent gas leaks from the body cavity. The seal may be in both the tool channel and the cable channel of the cannula. The cannula and the housings of the insertion tool may be made from medical grade plastic and have a paint finish on the housings. The cannula may have a semitransparent finish. The bottom of the insertion tool and the cannula may be made up of 2 black anodized simple machined parts.

Figure 6A:
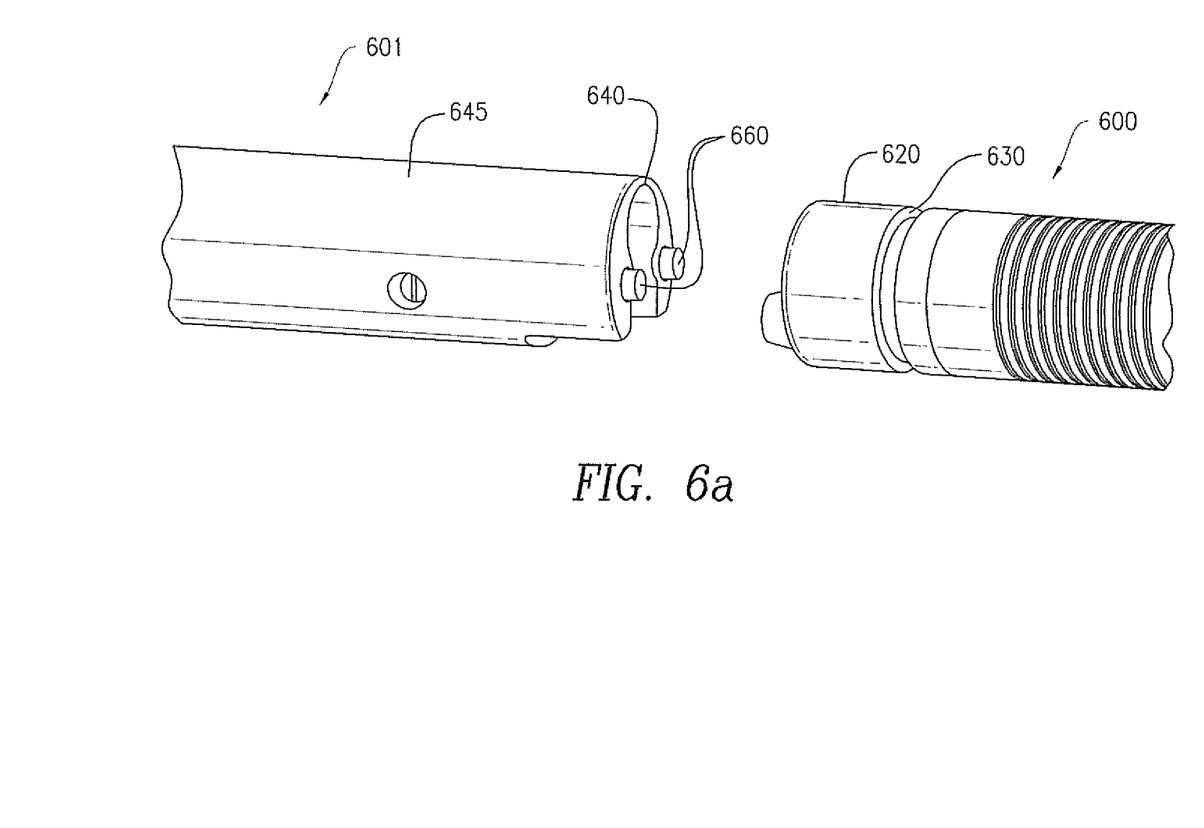
FIGS. 6a and 6b show the ends of the insertion tool and the insertable device for magnetic coupling.
Figure 6B:
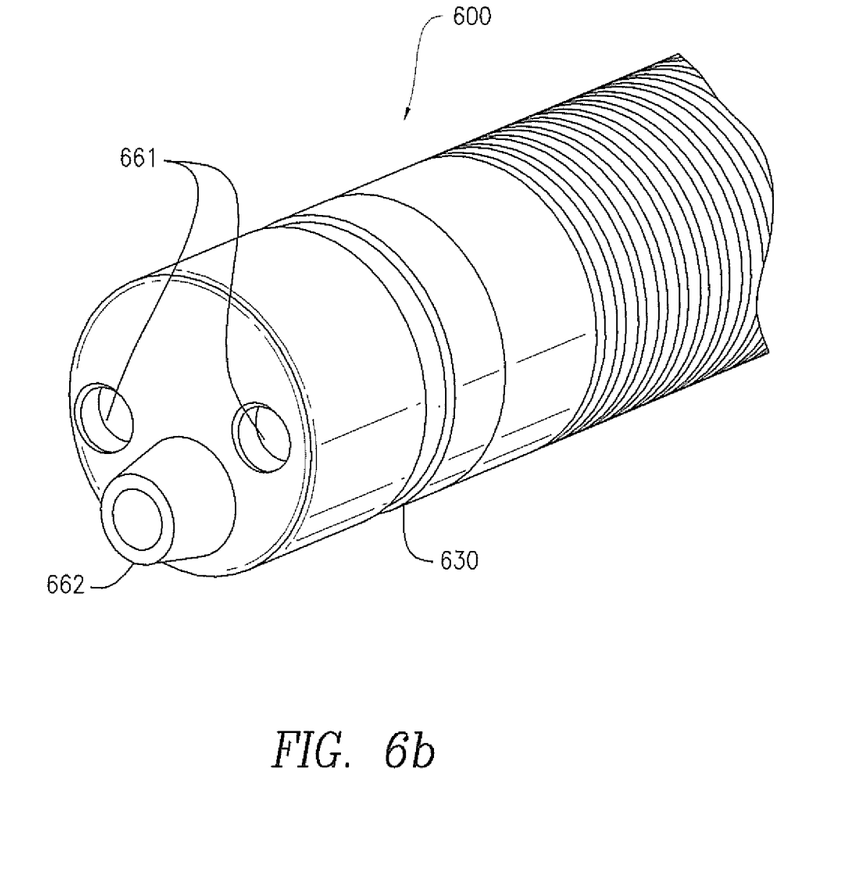

FIGS. 6a and 6b show the connection between insertable device 600 and insertion tool 601. Insertable device 600 is magnetically coupled to bottom 640 of insertion tool 601 with both bipolar magnetic couplers and mechanical couplers so that the external orientation of insertion tool 601 is always in the same orientation with insertable device 600. Insertion tool 601 and insertable device 600 are magnetically coupled, polarized, using 2 sets of magnets, 660, fitting male and female magnets at the end of insertion tool 601. Magnets 660 have a tunable pull force base on proximity magnets, 661. The mechanical coupling allows rotation of insertable device 600 without the potential for unwanted disconnect. Rear housing 620 of insertable device 600 provides grooves 630 for looping a snare. (There may be multiple grooves which can be located at multiple sites on the insertable device as needed to optimize the product.)

Insertion tool coupled with an insertable device is inserted into a body cavity through a standard laparoscopic trocar, 10 mm or 11 mm, for example. During insertion, the camera and the housing of the insertable device line up to form a cylinder (as shown in FIG. 1a). After insertion, the camera can be moved up and down or left and right in respect to the housing, as shown in FIG. 1b. The insertion tool can be rotated and manipulated to align the camera in the necessary position for performing surgery. The housing offset of the insertable device shows the position of the camera. While probing the body cavity for the best location to fix the insertable device, a "worm view" may be used. When positioning the camera, the camera may be positioned in an appropriate orientation of the horizon in the display of the image. Because of the coupling between the insertable device and the insertion tool, the horizon of the camera image does not change with the movement of the camera in the allowed directions.

Figure 7A:
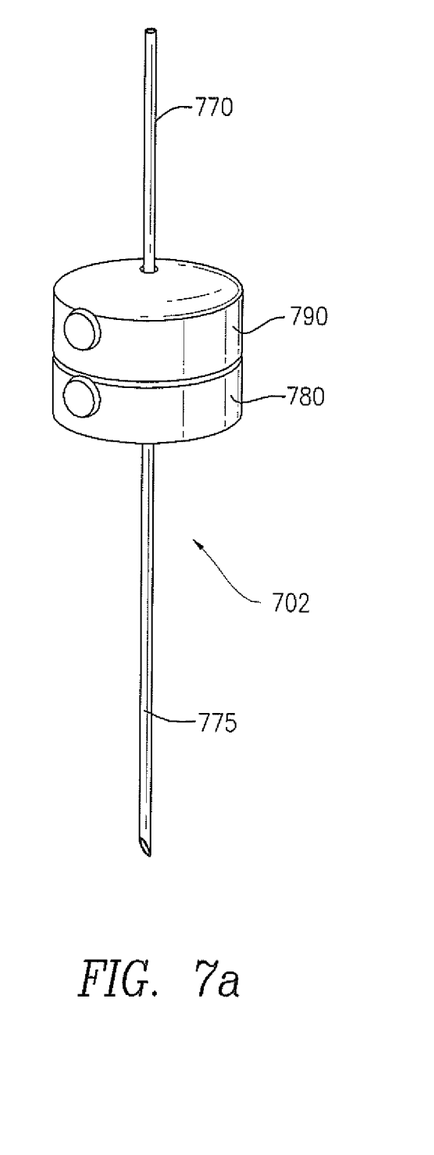
FIGS. 7a, 7b and 7c show a capture and fixation device of the present invention in different stages.
Figure 7B:
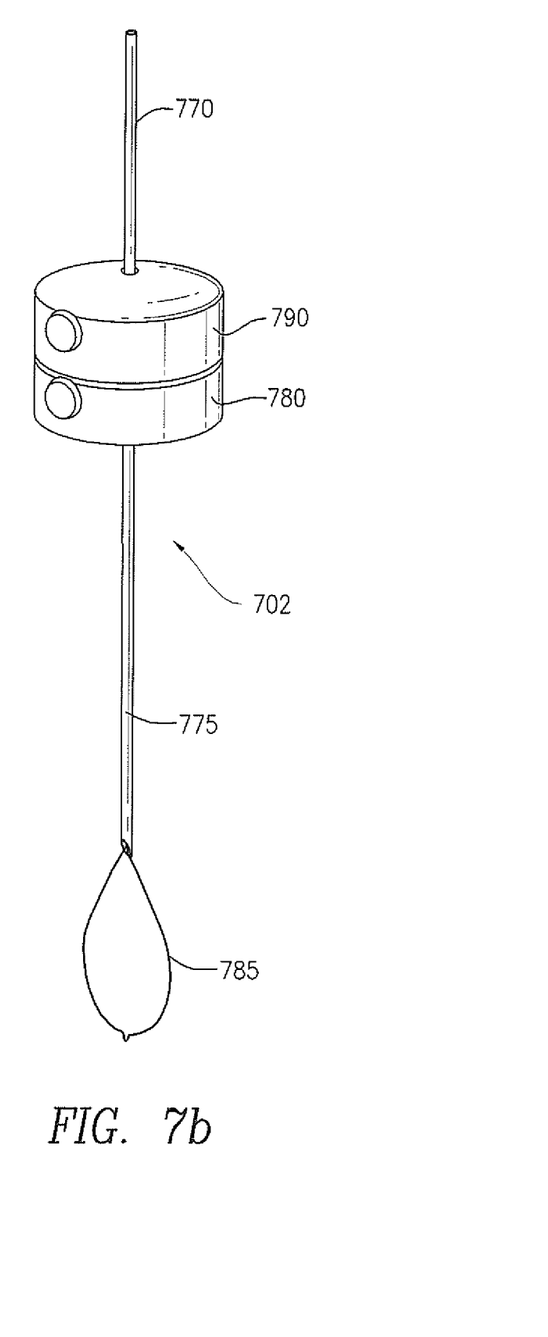

Once an insertable device is within the body cavity, it is captured and fixed in the optimal position by capture and fixation device 702. FIGS. 7a and 7b show capture and fixation device 702 which includes a long, hollow needle/cannula 775, at least two slidable clamp devices 780, 790, and a wire snare loop 785 that is deployable through plastic sheath 770 surrounding snare 785. Clamp mechanism 790 clamps and holds sheath 770 and wire snare 785 in the desired position within cannula 775. Clamp mechanism 780 slides along the outside of hollow needle/cannula 775 and holds needle/cannula 775 in a position so that snare 785 with insertable device 100 is firmly held up against the body cavity wall at the insertion site of needle/cannula 775 in the body cavity. Cannula 775 should have a maximum diameter of 3 mm to prevent visible scarring of the skin at the insertion site. A 3 mm cannula allows for a 2 mm working channel. Snare 785 may be oval, round, hexagonal, or other shape and is flexible so that it can conform to the shape of the camera module. FIG. 7a shows capture and fixation device 702 ready for insertion into a body cavity, for example the abdomen. In this position, snare 785 is retracted within cannula 775.

Figure 7C:
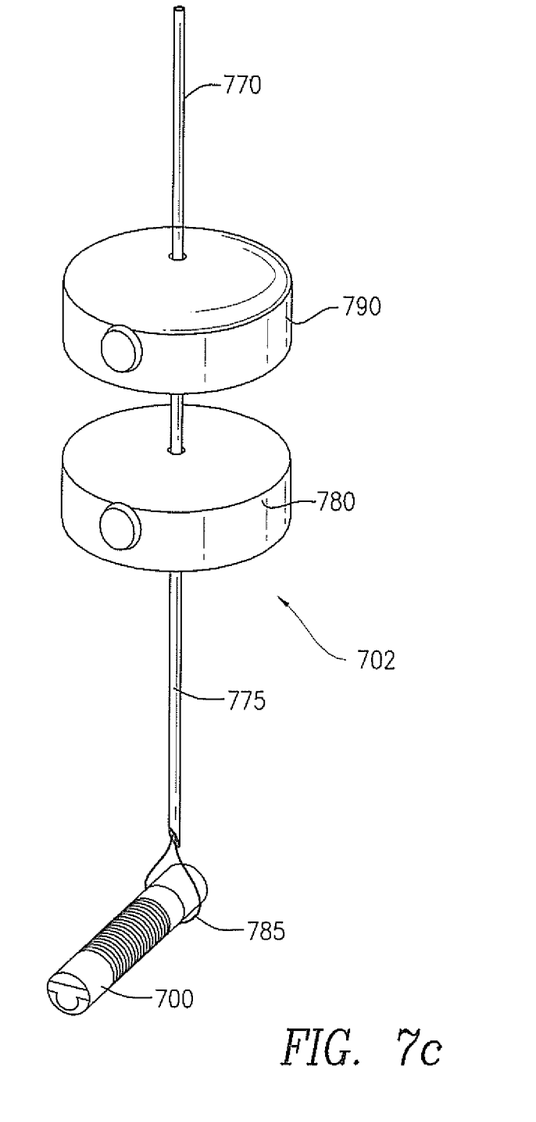

FIG. 7b shows the positioning of cannula 775 after it has been inserted into a body cavity and snare 785 is deployed. FIG. 7c shows capture and fixation device 702 positioned as if cannula 775 is inserted in the body cavity, insertable device 700 is captured by snare 785 and clamp 780 is deployed, clamping insertable device 700 against the cavity wall.

Figure 8:
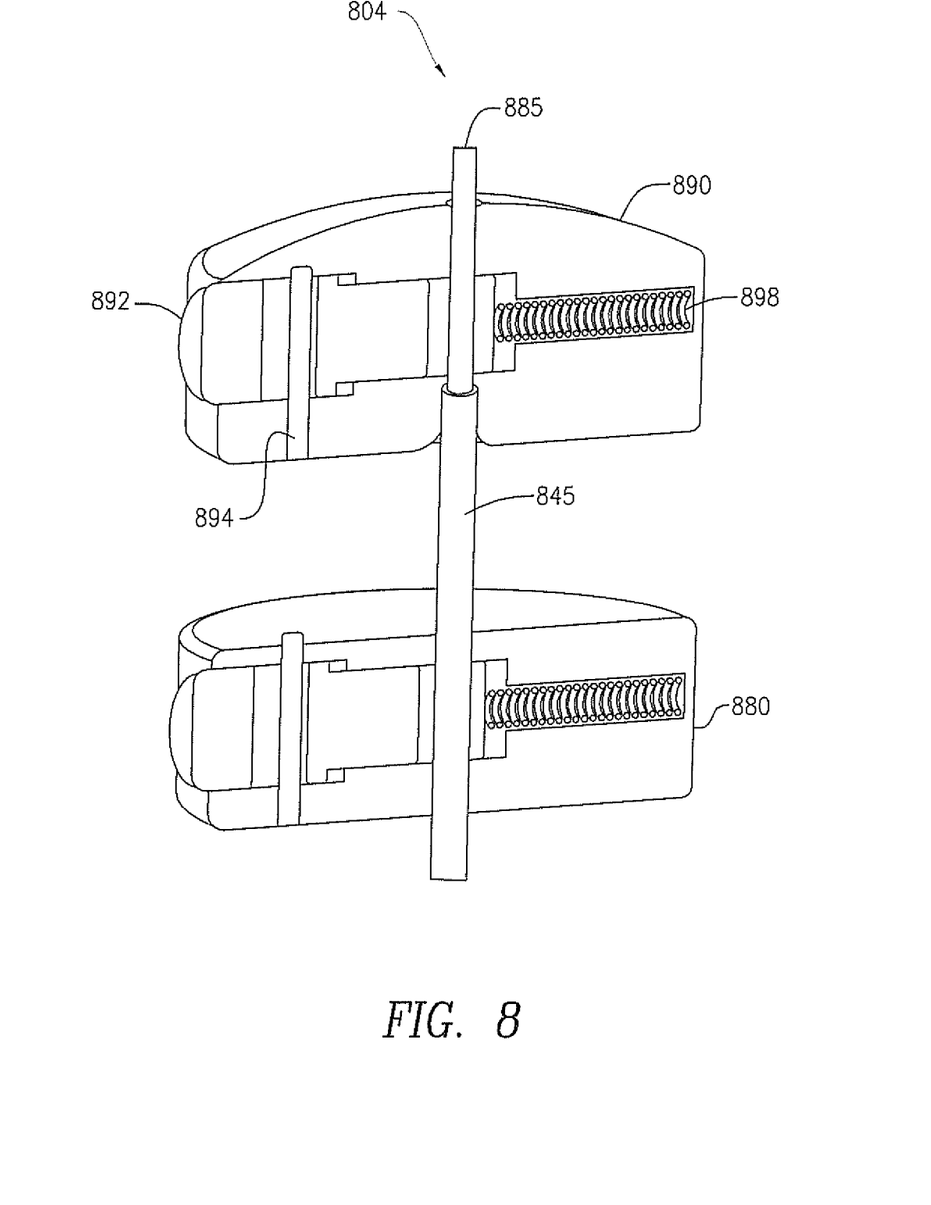
FIG. 8 shows a more detailed view of a clamp of the capture and fixation device of the present invention.

Upon insertion of an insertable device having a camera into a body cavity using the insertion tool, the capture and fixation device needle/cannula is inserted by a surgeon's assistant, for example, through the body wall using imaging from the camera of the insertable device. The needle/cannula is inserted through the body cavity wall with the snare retracted within the plastic sheath, and the plastic sheath residing within the cannula and not protruding during insertion of the cannula. After inserting the tip of the cannula into the body cavity using visualization from the camera on the insertable device, the tip of the plastic sheath is then advanced into the body cavity, followed by the snare which is deployed and opened in the body cavity. Using images from the camera, the insertable device is passed through snare 785 and snare 785 is then closed. The surgeon, for example, guides the insertable device through the snare with the imaging assistance provided by the insertable device camera. The snare is initially used to guide the insertable device into position. Once located in the desired field of view, the insertable device is pushed through the snare and tightened around the insertable device in a groove provided in the housing of the insertable device. The snare is then is pulled back through the needle/cannula until the insertable device is up against the end of the needle. Clamp, 790, in the handle of the needle/cannula 775 is then tightened to hold sheath 770 and snare 785 in that position. Needle 775 is withdrawn through the abdominal wall until the insertable device is adjacent to the interior side of the body cavity, for example, the abdominal wall. Clamp mechanism 780 is slid down needle 775 and positioned against the external surface of the body wall (skin) and allowed to tighten and hold the insertable device in the optimal position for surgery. FIG. 8 shows capture and fixation device 804 including snare 885, needle/cannula 845 and clamps 880, 890. Each clamp, a body clamp 880 and a snare sheath clamp, 890, may include a clamp button 892, a retention pin 894 and a clamp spring 898 as shown in FIG. 8.

Once insertable device is secured in the snare, the insertion tool is decoupled from the insertable device by pulling the insertion tool away from the now fixed insertable device to release the insertable device. The insertion tool is no longer attached to the insertable device, however the wires and tubes from the insertable device pass through one channel of the cannula of the insertion tool and the tool channel is now available for use in the procedure. The tool channel is used to introduce 3-5 mm laparoscopic instruments, for example, with which the operation can be performed.

The external electronics connected with the insertable device may include PC with GPU having a USB camera connector, an embedded Jetson board or other central processing unit for meeting computational requirements having both a local display and high resolution video outputs for connecting to one or more external displays, a surgical graphical user interface, a joystick interface, a trackball interface, or some other standard computer interface, an image processor and an image tracker.

Although the present invention has been described in conjunction with specific embodiments, those of ordinary skill in the art will appreciate the modifications and variations that can be made without departing from the scope and the spirit of the present invention. The capture and fixation device and insertion tool disclosed can be used for any insertable device in addition to the insertable device with a camera that is disclosed. Such modifications and variations are envisioned to be within the scope of the appended claims.

The invention claimed is:

1. A capture and fixation device for capturing and fixing an insertable device to an internal body cavity wall, the device comprising:
   a needle, wherein the needle inserts into and/or through a body cavity wall;
   a retractable loop and a plastic sheath located inside the needle, wherein the plastic sheath surrounds the retractable loop and the retractable loop is deployable through the plastic sheath passable through the needle, wherein the retractable loop is adapted to capture the insertable device once it is in the body cavity and retract into the needle to tighten around the insertable device,
   a first slideable clamp device located on the needle outside of the body cavity and adapted to clamp the sheath and the retractable loop in a position within the needle so the insertable device is up against an end of the needle; and
   a second slideable clamp device located on the needle outside of the body cavity and adapted to clamp the needle in a position holding the insertable device in the retractable loop so that the insertable device is fixed in a desired position near the body cavity wall.

2. The device as recited in claim 1 wherein the first slideable clamp device and the second slideable clamp device include a clamp button, a clamp spring, and a retention pin.

3. The device as recited in claim 1 wherein the retractable loop is adapted to rest in a groove in a housing of the insertable device.

4. The device as recited in claim 1 wherein the retractable loop is retracted in the needle upon insertion into the body cavity.

5. The device as recited in claim 1 wherein the retractable loop can be extended into a shape that surrounds the insertable device when deployed within the body cavity.

6. The device as recited in claim 1 wherein the desired location is against the body cavity wall.

7. The device as recited in claim 1 wherein the retractable loop, when extended, conforms to the shape of the insertable device when tightened around the insertable device.

8. The device as recited in claim 1 wherein once the insertable device is captured by the retractable loop, the first and second slideable clamp devices are adjusted to permit the needle to retract through the body cavity wall and the insertable device is adjacent an interior side of the body cavity wall.

9. The device as recited in claim 1 wherein the retractable loop is adapted to guide the insertable device into the desired position.

10. The device as recited in claim 1 wherein the first slideable clamp device is on an end portion of the needle.

11. The device as recited in claim 1 wherein the second slideable clamp device is slideable along the outside of the needle.

12. The device as recited in claim 1 wherein the second slideable clamp device is positioned against an external surface of the body cavity wall when fixing the insertable device in the desired position.

13. The device as recited in claim 1 wherein the needle has a maximum diameter of 3 mm.

14. The device as recited in claim 1 wherein the first slidable clamp device and the second slideable clamp device are spring loaded mechanisms.

* * * * *